United States Patent
Arcuri et al.

(10) Patent No.: US 7,423,187 B1
(45) Date of Patent: *Sep. 9, 2008

(54) RECOVERY OF TNT AND RDX FROM BULK COMPOSITION B EXPLOSIVES

(75) Inventors: Kym B. Arcuri, Tulsa, OK (US); Duane A. Goetsch, Andover, MN (US); Steve J. Schmit, Ramsey, MN (US); Ryan M. Smith, Minnetonka, MN (US); Paul Miller, Harvest, AL (US)

(73) Assignee: Gradient Technology, Elk River, MN (US)

( * ) Notice: Subject to any disclaimer, the term of this patent is extended or adjusted under 35 U.S.C. 154(b) by 665 days.

This patent is subject to a terminal disclaimer.

(21) Appl. No.: 10/796,956

(22) Filed: Mar. 10, 2004

Related U.S. Application Data

(60) Provisional application No. 60/453,304, filed on Mar. 10, 2003.

(51) Int. Cl.
*C07C 205/00* (2006.01)

(52) U.S. Cl. ..................... 568/935; 540/475

(58) Field of Classification Search ............... 568/935; 540/475
See application file for complete search history.

(56) References Cited

U.S. PATENT DOCUMENTS

| | | | |
|---|---|---|---|
| 5,977,354 A | * | 11/1999 | Spencer et al. ............. 540/475 |
| 5,990,357 A | | 11/1999 | Zawadiak et al. |
| 5,998,676 A | | 12/1999 | Arcuri et al. |
| 6,525,820 B1 | | 2/2003 | Owens |
| 6,777,586 B1 | | 8/2004 | Arcuri et al. |

* cited by examiner

*Primary Examiner*—Janet L. Andres
*Assistant Examiner*—Sudhakar Katakam
(74) *Attorney, Agent, or Firm*—Henry E. Naylor; Kean Miller Hawthorne D'Armond McCowan & Jarman LLP

(57) ABSTRACT

A continuous process for the separate recovery of TNT and RDX from a mixture of TNT and RDX. The mixture is introduced into a first vessel wherein TNT is separated from the RDX by use of a solvent that is effective for dissolving TNT but not RDX. The TNT in solvent is passed to a separation stage wherein the solvent is recovered a recycled to the first vessel. A slurry of RDX and water are passed to a second vessel where the water is displaced with a desensitizing agent for desensitizing RDX.

16 Claims, 1 Drawing Sheet

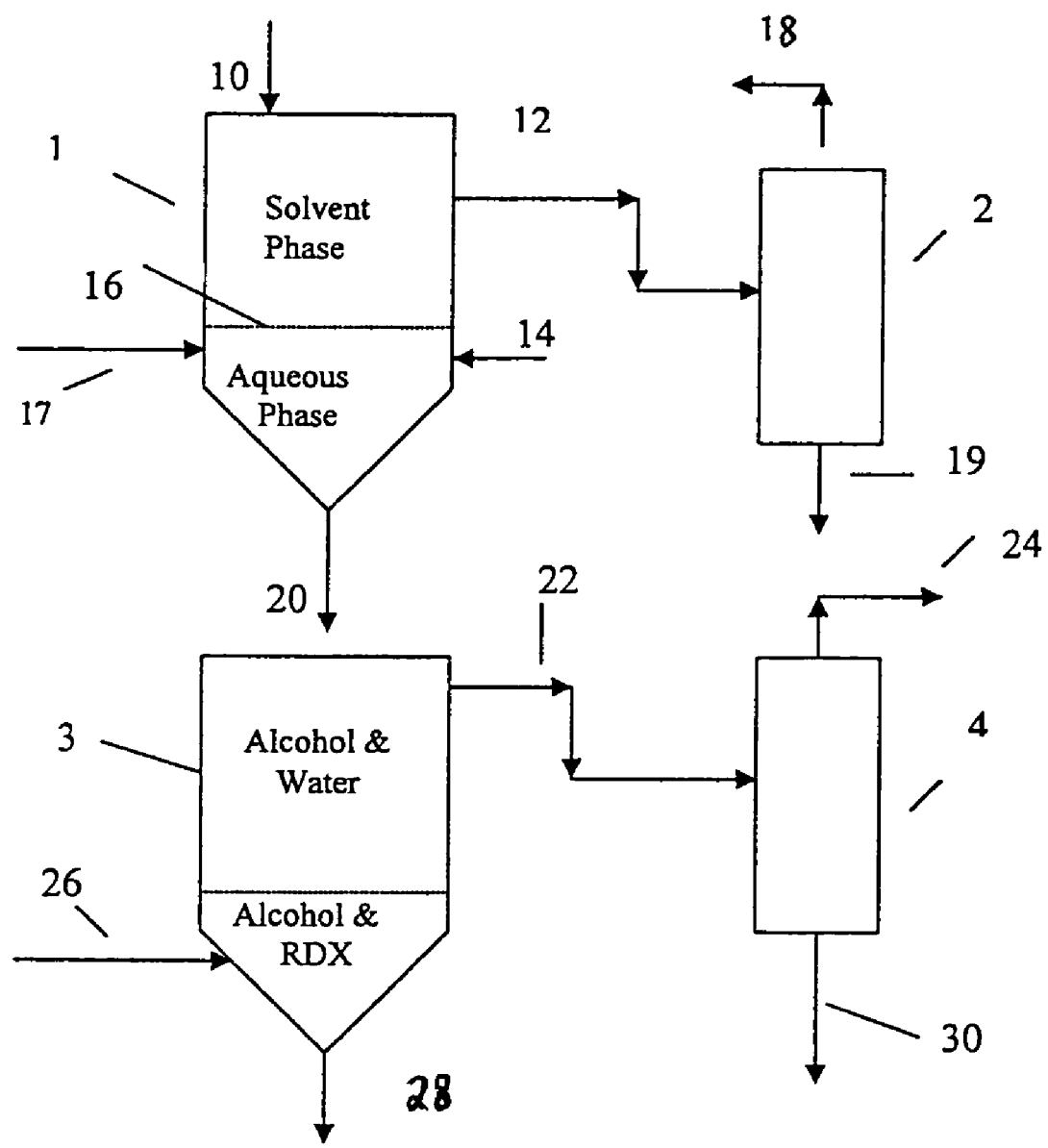

RECOVERY OF TNT AND RDX FROM BULK COMPOSITION B EXPLOSIVES

CROSS-REFERENCE TO RELATED APPLICATIONS

This application is based on Provisional Application 60/453,304 filed Mar. 10, 2003.

FIELD OF THE INVENTION

The present invention relates to a continuous process for the separate recovery of TNT and RDX from a mixture of TNT and RDX. The mixture is introduced into a first vessel wherein TNT is separated from the RDX by use of a solvent that is effective for dissolving TNT but not RDX. The TNT in solvent is passed to a separation stage wherein the solvent is recovered a recycled to the first vessel. A slurry of RDX and water are passed to a second vessel where the water is displaced with a desensitizing agent for desensitizing RDX.

BACKGROUND OF THE INVENTION

Surplus munitions, including bulk explosives, such as Composition B present a problem for the US military. Current budget constraints force the US military to prioritize its spending while effectively defending the interests of the United States. Defense budgets are further tightened because aging and surplus munitions must be guarded and stored. The US military regularly destroys a significant amount of its surplus munitions each year in order to meet its fiscal challenge. It also must destroy a significant amount of munitions each year due to deterioration or obsolescence.

In the past, munitions stocks have been disposed of by open burn/open detonation (OBOD) methods—the most inexpensive and technologically simple disposal methods available. Although such methods can effectively destroy munitions, they fail to meet the challenge of minimizing waste by-products in a cost effective manner. Furthermore, such methods of disposal are undesirable from an environmental point of view because they contribute to the pollution of the environment. For example, OBOD technology produces relatively high levels of $NO_x$, acidic gases, particulates, and metal waste. Incomplete combustion products can also leach into the soil and contaminate ground water from the burning pits used for open bum methods. The surrounding soil and ground water must often be remediated after OBOD to meet environmental guidelines. Conventional incineration methods can also be used to destroy munitions, but they require a relatively large amount of fuel. They also produce a significant amount of gaseous effluent that must be treated to remove undesirable components before it can be released into the atmosphere. Thus, OBOD and incineration methods for disposing of munitions become impractical owing to increasingly stringent federal and state environmental protection regulations. Further, today's ever stricter environmental regulations require that new munitions and weapon system designs incorporate demilitarization processing issues. Increasingly stringent EPA regulations will not allow the use of OBOD or excessive incineration techniques, so new technologies must be developed to meet the new guidelines.

Recovery and reuse methods, such as that of the present invention, are the most attractive alternative to the conventional destructive methods discussed above and can be used to recover, in an environmentally friendly way, substantially all of the munition components with very little waste generation. This state-of-the-art technology is feasible, safe, and relatively inexpensive. It also has the potential of meeting the recovery and reuse goals of demilitarization. Future demilitarization operations will be dominated by chemical conversion and recovery technologies that recover or convert the explosives and other components used in munitions manufacture to materials that can be recycled, or. resold, in a cost effective environmentally acceptable manner.

One type of explosive system that presents a demilitarization problem and in which the present invention can be practiced is bulk Composition B. That is Composition B that has not been loaded into a munition cavity, such as a shell casing. Composition B is a mixture comprised of 2,4,6-trinitrotoluene (TNT) and cyclo-1,3,5-trimethylene-2,4,6-trinitramine (RDX) powder with a binder which is typically wax. It is desirable to separate the TNT from RDX from Composition B for demilitarization purposes. U.S. Pat. No. 5,977,354 to Spencer et al. teaches a method for recovering RDX from TNT in explosives such as Composition B, and Cyclotol by heating the explosive composition to melt the TNT, separately collecting and recovering the melted TNT. The thus separated RDX material is contaminated with minor amounts of TNT is treated with a solvent for TNT and a non-solvent for RDX to dissolve the TNT.

While the above Spencer patent presents an approach to recovering TNT from RDX there is never-the-less a need in the art for a continuous process for separately recovering TNT and RDX from bulk Composition B that contains RDX, TNT and a binder.

SUMMARY OF THE INVENTION

In accordance with the present invention there is provided a process for recovering TNT and RDX from a blend of TNT and RDX, which process comprises:

a) conducting said blend of TNT and RDX into the upper section of a contact vessel containing a solvent phase at its upper section and a water phase at its lower section wherein solvent is continuously introduced into said vessel above the water phase and wherein water is continuously introduced into said vessel to maintain a predetermined level;

b) dissolving at least a portion of the TNT in the solvent phase, thereby resulting in a solvent/TNT solution and wherein solid RDX particles settle through the solvent phase and into the water phase resulting in an upper solvent/TNT phase and a lower RDX solids/water slurry phase;

c) conducting said solvent/TNT solution from said contact vessel to a separation zone wherein solvent is separated from said TNT and wherein said solvent is recovered separately from the TNT;

d) conducting said RDX solids/water slurry to a recovery vessel that contains a desensitizing agent effective for desensitizing the RDX, wherein said desensitizing agent is continuously introduced into said recovery vessel;

e) displacing said water in said slurry with said desensitizing agent to result in an upper water/desensitizing agent phase and a lower RDX solids/desensitizing agent phase;

f) collecting said RDX solids/desensitizing agent phase; and g) conducting said water/desensitizing agent phase to a separation zone wherein the water is separated from the desensitizing agent.

BRIEF DESCRIPTION OF THE FIGURES

The sole FIGURE hereof shows a preferred process scheme wherein TNT and RDX are recovered separately from bulk Composition B explosive material.

DETAILED DESCRIPTION OF THE INVENTION

The Composition B explosive material that is preferred for the practice of the present invention will be a bulk material comprised of a mixture of 2,4,6-trinitrotoluene (TNT) with cyclo-1,3,5-trimethylene-2,4,6-trinitramine (RDX) particles with a binder. The binder will preferably be a wax. The typical amount of TNT found in Composition B is at least about 35 wt. %, preferably at least about 40 wt. %, more preferably greater than 50 wt. %, and even as high as 4:1 TNT to RDX. One specific Composition B composition contains about 39.5 wt. % TNT and 59.5 wt. % RDX comprising the energetic component with wax as a binder. By "bulk" we mean that the Composition B to be treated in accordance with the present invention is not contained in a munition cavity, such as a military shell, which is usually in the form of a warhead, bomb, or projectile. Military shells present another set of problems for recovering RDX is substantially pure form because of the presence of an organic liner in the shell, which liner is typically comprised of asphalt.

In the practice of the present invention TNT and RDX powder are recovered as valuable discrete commercial products. Conventional methods for disposing of Composition B-containing military shells, such as incineration, chemical degradation, and detonation are not capable of recovering the TNT and RDX powder as discrete components.

Reference is made to the sole FIGURE hereof which represents one preferred process scheme for practicing this invention. A blend of TNT and RDX, preferably in the form of Composition B, is continuously conducted via line 10 into vessel 1 where it is contacted with a solvent in which TNT is effectively soluble and in which RDX is substantially insoluble. It will be understood that the, vessel can be of any suitable configuration or size depending on the volume of material to be processed. For example, the vessel can be a tank or conduit suitable for processing material in slurry form. The solvent is chosen so that the binder, preferably a wax, and more preferably a natural wax such as bees wax, is also substantially soluble in the solvent. The solvent should have sufficient polarity to allow dissolution of the TNT while not dissolving significant quantities of RDX. A most preferred solvent is one in which TNT is readily soluble at room temperature (22° C.) and in which RDX is substantially insoluble. Solvents with these quantities will have limited solubility towards the wax binder present in Composition B. Lower vapor pressure solvents that are immiscible with water are preferred. Types of solvents preferred for dissolving TNT in the practice of the present invention include aromatics having alkyl side chains of which toluene is the more preferred. For one skilled in the art, other solvents or mixtures of solvents can be employed providing the aforementioned properties are met.

The solvent can be introduced either with the Composition B via line 10 or preferably via line 17. Water is introduced into vessel 1 via line 14 and maintained at a level 16 so that below that level is an aqueous phase containing RDX solids and above that level is an organic, or solvent phase containing dissolved TNT and some wax. The Composition B will be in contact with the solvent for an effective amount of time. That is, for at least that amount of time wherein substantially all of the TNT is dissolved in the solvent. This amount of time is determined by the net velocity of the Composition B as it is introduced into vessel 1 via line 10. The amount of solvent employed per unit mass of Composition B fed into vessel 1 is determined by a number of factors but is bounded by the velocity of the net flow to the solvent/TNT outlet at line 12. The solvent introduced into vessel 1 via line 17 travels through the vessel at a given velocity defined by the solvent volumetric flow rate divided by the open cross sectional area of the contact volume. If this velocity exceeds the settling velocity of the Composition B solids, or RDX crystals, settling within the aqueous phase will be limited and solids will undesirably be swept out with the solvent/TNT solution at line 12. The settling velocity of the solids, which is typically in the form of flakes, will vary from about 0.5 cm/second to about 5 cm/sec, or higher depending on the particle size of the Composition B solids fed into vessel 1 and the particle size of the resulting RDX crystals. It will be understood that RDX solids, RDX particles, and RDX crystals are used interchangeably herein.

Dissolution of the TNT in typical bulk flakes will usually occur within a time span of about 20 to 60 seconds. The precise amount of time of course will be dependent upon such things as the temperature at which vessel 1 is maintained. This temperature will range from about ambient temperature to about 80° C. Preferred temperatures will be from about 20° C. to about 80° C., preferably from about 20° C. to about 70° C., and more preferably from about 25° C. to about 50° C. By ambient temperature we mean the temperature of the environment of the vessel, without the addition of heat. Such ambient temperatures will typically be from about 20° C. to about 30° C. As the TNT and binder dissolve in the solvent the RDX particles will settle from the solvent phase to the aqueous phase. As previously mentioned, the rate at which solvent is introduced into vessel 1 will be less than the settling velocity of the solids within the vessel. Consequently, the geometry and volume of vessel 1 depends on the throughput, average RDX particle size, and allowable headspace and footprint appropriate for the operating area. Vessel 1 can be designed to allow solid flow along an incline created by internal baffles. These baffles increase the contacting time between the solvent and solids and minimize the potential passage of RDX or Composition B particles out of the vessel with the solvent/TNT.

While it is preferred that substantially all of the binder (for example wax) material dissolve in the solvent in vessel 1, for practical purposes the amount of solvent or the contacting time necessary for complete dissolution of the binder may prove to be impractical. In cases where the amount of solvent in vessel 1 is insufficient to completely dissolve the binder, some of the binder material will adhere to the RDX particles and pass through the organic phase into the aqueous phase.

Vessel 1 in this example contains a cone shaped bottom section or any other appropriate geometric shape that will permit the RDX particles to settle to a sufficient depth thereby packing the RDX particles and minimize water contained within the resulting inter-particle voids. A preferred geometry will be a cone shape with an approximate 65-70° angle (from the horizontal to the straight side vessel wall). The amount of water contained within vessel 1 is minimized by the use of a suitable measuring device, such as a capacitance probe that monitors the maximum allowable depth of water from the base of the cone and the maximum allowable height (or volume of water). The maximum allowable height is based on minimizing the amount of water discharged with the collected RDX particles and the volume inventory of RDX within the vessel.

The solvent solution-containing the dissolved TNT and binder is continuously removed from vessel 1 via line 12. Line 12 is positioned at an effective distance from the aqueous phase to prevent the migration of Composition B and RDX particles to line 12. The solvent/TNT solution exits vessel 1 via line 12 and is conducted into vessel 2, which can also be referred to as the primary solvent recovery vessel. This vessel can be a simple flash drum wherein the solvent is flash evaporated from the dissolved TNT and binder and drawn over head via line 18 for storage and/or recycle to vessel 1. Reduced pressures may also be used in the recovery vessel to facilitate vaporization of the solvent. Any suitable alternate method can be used for crystallizing (recovering) the TNT. Non-limiting examples of such alternate methods include cooling to subambient temperatures. The solid TNT particles settle in vessel 2 and a water phase at the bottom of this vessel (not shown) can be used to separate the settled TNT crystals from the solvent solution. There will typically be some TNT contained in the solvent recycled to vessel 1 via line 18 when using cooling to recover the TNT from the solvent The settled TNT in vessel 2 can be passed on, via line 19, for either collection or to a melt kettle for drying and recovery by use of traditional TNT handling procedures, such as by passing it to a belt flaker for final product delivery. If the TNT collected in vessel 2 contains excessive binder the TNT/water slurry can be transferred to a third contacting vessel (not shown) where the TNT/water slurry is contacted with a solvent such as acetone that is effective for dissolving the TNT but not the binder. The TNT will dissolve in the solvent leaving behind the binder as a solid. The binder can be removed through the use of any suitable of solid/liquid separation method. The TNT can then be recovered by any suitable means, such as by re-crystallization using either flashing, sub ambient cooling, or water addition. The recovered TNT crystals can then be dried using conventional methods used to prepare high purity TNT flakes.

The acetone and water can be separated using a distillation step and recovered for re-use. Trace quantities of RDX in the water phase can be eliminated through the use of a mild caustic or comparable basic wash.

The aqueous slurry of RDX particles and water exit vessel 1 via line 20 and is conducted into vessel 3 wherein the water is displaced with a suitable desensitizing agent that is effective to desensitize the RDX for safe handling. The desensitizing agent will typically be an alcohol, preferably isopropyl alcohol. The RDX particles settle to the bottom to the alcohol phase. Water and alcohol are drawn off via line 22 to separation vessel 4 wherein the alcohol is separated by either flashing or distillation and stored and/or recycled. The water, which is collected via line 30 can also be recycled if desired. The RDX/water slurry is removed from vessel 1 either continuously or in semi-batch mode. In order to maximize the throughput efficiency the TNT dissolved in the toluene is removed continuously and the RDX can be removed incrementally keeping the minimum amount of toluene within vessel 1 to ensure substantial complete dissolution of the TNT.

It is preferred that the RDX/water slurry be contacted with the desensitizing agent (isopropyl alcohol) in a counter-current mode or in a series of contacting/settling vessels in order to minimize the amount of the water/desensitizing agent resulting after water displacement.

The settled RDX particles may contain unacceptable levels of residual binder, or wax, that was not completely dissolved during contact with the solvent in vessel 1. The extent of solvent contacting can be extended in an attempt to reduce the wax levels to acceptable values, however this is not always the preferred solution. Complete dissolution of the wax within the toluene may require excessive volumes and/or an unacceptable vessel height or volume. In addition to residual wax there may be other solids introduced during various stages of explosive handling. These "other solids" are referred to as foreign solids within the RDX slurry. These include dirt, grime and other toluene insoluble solids, which can settle with the RDX.

Unacceptable levels of residual wax and/or the presence of other toluene insoluble solids can adversely affect the purity of the recovered RDX. Consequently additional processing may be necessary to ensure RDX quality.

Residual wax can be removed by contacting the RDX with aliphatic type solvent such as hexane, nonane or mixtures thereof. Any linear or branched paraffin is acceptable. The preferred solvent should be one, which can be readily separated from the wax using distillation or a flash type process. The RDX/water slurry is sent to a contacting tank containing a solvent that can readily dissolve the wax. The slurry is introduced at the top of the column and allowed to settle through the solvent. The wax will separate fro the RDX particles and dissolve into the solvent. Both the water and RDX will settle at the bottom of the solvent contacting vessel. The solvent contacting step precedes contacting with isopropyl-alcohol.

Under conditions where the RDX contains both unacceptable levels of wax and/or foreign solids, which are toluene insoluble, it may be necessary to dissolve and re-crystallize the RDX. There may be situations in which a change in the RDX particle size is warranted. Dissolving and re-crystallizing offers the opportunity to change both the size and morphology of the RDX crystals.

In these cases, the RDX/water slurry recovered after contacting with toluene is sent to an acetone contacting vessel. The quantity of acetone needed is that required to completely dissolve the RDX. The dissolved RDX is than passed through a volume, which permits the acetone insoluble material to settle out (this includes residual wax and foreign solids). The solid and wax free RDX/acetone solution is then contacted with sufficient water to allow recrystallization of the RDX. Both temperature, residence time, and the mixing characteristics of the re-crystallization vessel are adjusted to allow the nucleation and growth of the desired particle size and morphology.

What is claimed is:

1. A process for separately recovering 2,4,6-trinitrotoluene and cyclo-1,3,5-trimethylene-2,4,6-trinitramine from a blend of 2,4,6-trinitrotoluene and cyclo-1,3,5-trimethylene-2,4,6-trinitramine, without melt-out of the 2,4,6-trinitrotoluene, which process comprises:

a) conducting said blend of 2,4,6-trinitrotoluene and cyclo-1,3,5-trimethylene-2,4,6-trinitramine into the upper section of a contact vessel containing a solvent phase at its upper section and a water phase at its lower section wherein solvent is continuously introduced into said vessel above the water phase and wherein water is continuously introduced into said vessel to maintain a predetermined level;

b) dissolving at least a portion of the 2,4,6-trinitrotoluene in the solvent phase, thereby resulting in a solvent/2,4,6-trinitrotoluene solution and wherein solid cyclo-1,3,5-trimethylene-2,4,6-trinitramine particles settle through the solvent phase and into the water phase resulting in an upper solvent/2,4,6-trinitrotoluene phase and a lower cyclo-1,3,5-trimethylene-2,4,6-trinitramine solids/water slurry phase;

c) conducting said solvent/2,4,6-trinitrotoluene solution from said contact vessel to a separation zone wherein solvent is separated from said 2,4,6-trinitrotoluene and wherein said solvent is recovered separately from the 2,4,6-trinitrotoluene;

d) conducting said cyclo-1,3,5-trimethylene-2,4,6-trinitramine solids/water slurry to a recovery vessel that contains a desensitizing agent effective for desensitizing the cyclo-1,3,5-trimethylene-2,4,6-trinitramine wherein said desensitizing agent is continuously introduced into said recovery vessel;

e) displacing said water in said slurry with said desensitizing agent to result in an upper water/desensitizing agent phase and a lower cyclo-1,3,5-trimethylene-2,4,6-trinitramine solids/desensitizing agent phase;

f) collecting said cyclo-1,3,5-trimethylene-2,4,6-trinitramine solids/desensitizing agent phase; and g) conducting said water/desensitizing agent phase to a separation zone wherein the water is separated from the desensitizing agent.

2. The process of claim 1 wherein there is also a binder present with the blend of 2,4,6-trinitrotoluene and cyclo-1,3,5-trimethylene-2,4,6-trinitramine.

3. The process of claim 2 wherein said binder is a wax.

4. The process of claim 1 wherein said solvent is toluene.

5. The process of claim 1 wherein substantially all of the 2,4,6-trinitrotoluene is dissolved in said solvent.

6. The process of claim 3 wherein substantially all of the 2,4,6-trinitrotoluene is dissolved in said solvent.

7. The process of claim 1 wherein the solvent is introduced into said contact vessel at a rate lower than the rate of settling of said particles.

8. The process of claim 6 wherein the solvent is introduced into said contact vessel at a rate lower than the rate of settling of said particles.

9. The process of claim 1 wherein the solvent is recycled to said contact vessel after being separated from said 2,4,6-trinitrotoluene.

10. The process of claim 8 wherein the solvent is recycled to said contact vessel after being separated from said 2,4,6-trinitrotoluene.

11. The process of claim 1 wherein said desensitizing agent is introduced into said recovery vessel countercurrent to the introduction of said cyclo-1,3,5-trimethylene-2,4,6-trinitramine solids/water slurry.

12. The process of claim 10 wherein said desensitizing agent is introduced into said recovery vessel countercurrent to the introduction of said cyclo-1,3,5-trimethylene-2,4,6-trinitramine solids/water slurry.

13. The process of claim 1 wherein said desensitizing agent is recycled to said recovery vessel after being separated from the water.

14. The process of claim 12 wherein said desensitizing agent is recycled to said recovery vessel after being separated from the water.

15. The process of claim 1 wherein said desensitizing agent is isopropyl alcohol.

16. The process of claim 12 wherein said desensitizing agent is isopropyl alcohol.

* * * * *